US012642895B2

(12) United States Patent
Wadhwa et al.

(10) Patent No.: US 12,642,895 B2
(45) Date of Patent: Jun. 2, 2026

(54) BREAST PUMP SYSTEM AND A PUMP ARRANGEMENT FOR A BREAST PUMP SYSTEM

(71) Applicant: KONINKLIJKE PHILIPS N.V., Eindhoven (NL)

(72) Inventors: Sahil Wadhwa, Venlo (NL); Johannes Petrus Antonius Maria Van Asseldonk, Best (NL); Coen Petrus Martinus Claassen, Lommel (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 904 days.

(21) Appl. No.: 17/780,200

(22) PCT Filed: Dec. 8, 2020

(86) PCT No.: PCT/EP2020/084966
§ 371 (c)(1),
(2) Date: May 26, 2022

(87) PCT Pub. No.: WO2021/122123
PCT Pub. Date: Jun. 24, 2021

(65) Prior Publication Data
US 2022/0409781 A1 Dec. 29, 2022

(30) Foreign Application Priority Data
Dec. 19, 2019 (EP) ..................................... 19217961

(51) Int. Cl.
*A61M 1/06* (2006.01)
*F04B 17/03* (2006.01)
*F04B 53/00* (2006.01)

(52) U.S. Cl.
CPC ............. *A61M 1/062* (2014.02); *F04B 17/03* (2013.01); *F04B 53/003* (2013.01); *A61M 2205/42* (2013.01)

(58) Field of Classification Search
CPC ............................................. A61M 1/06–0697
See application file for complete search history.

(56) References Cited

U.S. PATENT DOCUMENTS 7,438,706 B2 10/2008 Koizumi
2001/0038799 A1* 11/2001 Silver ..................... A61M 1/06
417/474

(Continued)

FOREIGN PATENT DOCUMENTS

CA 3015141 A1 9/2017
CN 110107477 A 8/2019

(Continued)

OTHER PUBLICATIONS

English Translation of WO 201509934 (Guo) (Year: 2015).*

(Continued)

*Primary Examiner* — Courtney B Fredrickson

(57) ABSTRACT

A pump arrangement is provided for a breast pump system having a pump motor assembly and a damping arrangement, providing a coupling between an outer surface of the pump motor assembly and an inner surface of a housing for the pump arrangement. A set of one or more limbs extends outwardly from a frame. For example, cushions are formed by a pair of radially extending limbs and a connecting piece connecting to the pair of limbs. This arrangement provides positioning within the housing as well as damping.

13 Claims, 9 Drawing Sheets

(56)         References Cited

U.S. PATENT DOCUMENTS

2019/0365966  A1      12/2019  Bachler
2020/0254159  A1       8/2020  Van Asseldonk

FOREIGN PATENT DOCUMENTS

EP          0749328  B1      4/2003
EP          2196229  A1      6/2010
EP          2376138  B1      4/2016
EP          2825220  B1     12/2017
EP          3131599  B1      2/2019
KR       20150001238  U      3/2015
WO      WO-2015109934  A1  *  7/2015   .............. A61M 1/06

OTHER PUBLICATIONS

International Search Report and Written Opinion Dated Mar. 5, 2021 for International Application No. PCT/EP2020/084966 Filed Dec. 8, 2020.

* cited by examiner

BREAST PUMP SYSTEM AND A PUMP ARRANGEMENT FOR A BREAST PUMP SYSTEM

CROSS REFERENCE TO RELATED APPLICATIONS

This application is the U.S. National Phase application under 35 U.S.C. § 371 of International Application No. PCT/EP2020/084966 filed Dec. 8, 2020, which claims the benefit of European Patent Application Number 19217961.2 filed Dec. 19, 2019. These applications are hereby incorporated by reference herein.

FIELD OF THE INVENTION

This invention relates to breast pump systems.

BACKGROUND OF THE INVENTION

A breast pump system typically comprises an expression unit and pump arrangement which are connected via a tube. The pump arrangement comprises one or more motors within a housing to drive a pump or pumps (e.g. one pump or one pump for each breast) and deliver a vacuum (suction) pressure to the expression unit.

The pump motor or motors need to be suspended by flexible elements to isolate vibrations and noise that may otherwise emanate to the housing and the environment.

Current suspensions require a lot of space around the pump motor or motors and are costly to make due to the typical use of steel springs. Springs are also known to be hard to assemble, and do not usually provide a controlled integrated end-stop to movement.

US 2019/365966 discloses a medical suction pump in which a motor is fitted in a seat, and that seat couples to elastic sound absorbing bearings.

EP 2 196 229 discloses a motorized head for a breast pump with a vibration absorbing member within a mounting portion for a motor.

KR 2015/0001238 discloses a frame mounted at the output face of a motor, having supporting legs.

CN 110 107 477 discloses a motor with a mounting suspension for coupling the motor to a frame at each end.

It would therefore be desirable to provide a lower cost and easier to assemble damping system for the pump motor or motors.

SUMMARY OF THE INVENTION

The invention is defined by the claims.

According to examples in accordance with an aspect of the invention, there is provided a pump arrangement for a breast pump system, comprising:

a housing;

a pump motor assembly comprising a pump motor with an axis or a set of one or more pump motors with parallel axes; and a damping arrangement coupled to the pump motor assembly providing a coupling between an outer surface of the pump motor assembly and an inner surface of the housing, wherein the damping arrangement comprises:

a frame for coupling to the pump motor assembly, wherein the frame comprises a ring arrangement which:

extends around the pump motor; or extends around each pump motor of the set; or extends around the overall assembly of the set of pump motors, and wherein the frame extends in a plane perpendicular to the axis or set of parallel axes; and a set of one or more first limbs extending at least partially radially outwardly from the axis or one of the set of parallel axes from the outside of the frame.

This pump arrangement has one or more pump motors. Attached to the set of pump motors is a damping arrangement. The damping arrangement is generally between the set of pump motors and the housing. There may be only one connection from the pump motor assembly to the damping arrangement, even if there are multiple pump motors, for example because multiple pump motors may be connected together as a single assembly. This damping arrangement may have a single frame shaped to surround or attach to the overall pump motor assembly (whether there is one or a set of multiple pump motors) or it may be a set of frame portions, with one for each pump motor.

This design avoids the need for metal springs as the first limbs provide the damping. The first limbs suspend the pump motor assembly such that there is no other direct connection that can transmit sound between the pump motor assembly and the housing. The assembly is easy to assemble because the frame fits around or to the set of pump motors.

There may further be a set of one or more second limbs extending at least partially radially outwardly from the outside of the frame, wherein there is a connecting piece between pairs of first and second limbs spaced apart around the frame, such that a pair of first and second limbs and associated connecting piece form a cushion. Thus, each cushion comprises a pair of limbs between which a connecting piece extends. The connecting piece couples the limbs together to function as a unit.

The cushion or cushions again reduce the amount of space required compared to a steel spring. At the same time, the cushion or cushions may be formed of electrically and thermally insulating material giving additional insulating material properties. The damping performance of the cushions may be easier to control and the structure may be easier to manufacture that freely suspended limbs.

The collapse of the cushions, in particular the first and second limbs, provides an end stop feature to ensure that the suspended mass of the pump motor assembly does not cause further damage to other components in the assembly or create loud impact noises every time the pump arrangement faces accelerations when being moved around. The cushion or cushions, in particular the limb or limbs of the cushion or cushions, can for example simply collapse on themselves to provide this end stop.

The combination of the material of the limb and/or cushions and the specific design of the limb or limbs can be selected to result in specific stiffness and therefore the damping properties can be tuned to the specific mass of the pump motor assembly and other suspended parts.

A single frame may be designed to optimize the assembly process to save assembly time and cost compared to the assembly of multiple steel springs. The use of separate multiple frames may give more design freedom.

The frame may couple directly to the pump motor or motors or it may couple to a chassis which supports the pump motor or motors. Furthermore, the frame may also couple to other components such as a battery.

The first and second limbs are preferably arcuate. This means they can bend to collapse.

Each limb is for example C-shaped, with the open sides of a pair of C-shaped limbs of one cushion facing each other.

Each limb may instead be S-shaped. Any arcuate shape may however be employed which gives a predictable compression response.

The radial outermost ends of the limbs may each comprise an alignment feature for aligning with a corresponding alignment feature of the inner surface of the housing. In this way, the limbs provide positioning of the pump arrangement within the housing.

The set of cushions may comprise a set of four cushions. These may for example define corners of a rectangle so that damping is provided in all directions in the plane perpendicular to the elongate axes.

The frame comprises a ring arrangement. The ring arrangement may comprise a respective ring around each pump motor (either directly around the pump motor or around a chassis holding the pump motor) of the set of one or more pump motors and extending around the axis of the respective pump motor. Thus, separate rings may be provided, as mentioned above, and their limbs and/or cushions combine to form an overall damping arrangement or an overall cushion arrangement.

The ring arrangement then has a ring for each pump motor (for fixing that ring to that pump motor) and a set of first limbs or a set of cushions. All of the first limbs or cushions may be around a single ring if there is only one ring, or there may be first limbs or cushions on multiple rings, which together form the damping arrangement.

Each cushion is for example a cavity structure with sides (the limbs) and a top (the connecting piece). The cavity structure provides a damping function. The limbs function as locating elements for setting the position of the pump arrangement within the housing.

Each connecting piece is for example radially spaced from the outside of the frame (i.e. the respective ring). This forms a cavity between the frame and the connecting piece, which functions as a damping structure. The damping arrangement is for example made of a rubber.

The frame is for example made of a rubber or rubber-like material. It may be any suitable elastically deformable material. It can have its material, shape and thickness selected to provide the desired damping.

Each cushion may comprise a stopper formed between the frame (i.e. the ring) and the connecting piece. This may be used to set the collapse state of the cushion, without requiring any additional parts.

The pump arrangement may comprise two pump motors, each with a ring with two cushions, such that the pump arrangement has four cushions arranged at corners of a rectangle.

The pump arrangement may have an inlet conduit and an outlet conduit, wherein the inlet and outlet conduits extend parallel to the axes and provide positioning of the pump arrangement in a direction parallel to the elongate axes.

The damping arrangement in particular provides control of damping in a plane perpendicular to the elongate axes. The use of the conduits to provide positioning in the direction parallel to the elongate axes prevents contact with the housing in that direction and provides vibration damping for the parallel direction.

The ring arrangement may extend around a main body of the pump motor, or around a main body of each pump motor of the set, or around the main bodies of the overall assembly of the set of pump motors. For example, the (or each) pump motor may have opposite end walls (though which electrical connections or a mechanical output drive shaft may pass). The frame may comprise a ring located between one quarter and three quarters of the way along the pump motor main body between the end walls. The end walls are for example circular and the connecting wall between them is cylindrical.

The invention also provides a breast pump system comprising:

an expression unit; and a pump arrangement as defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
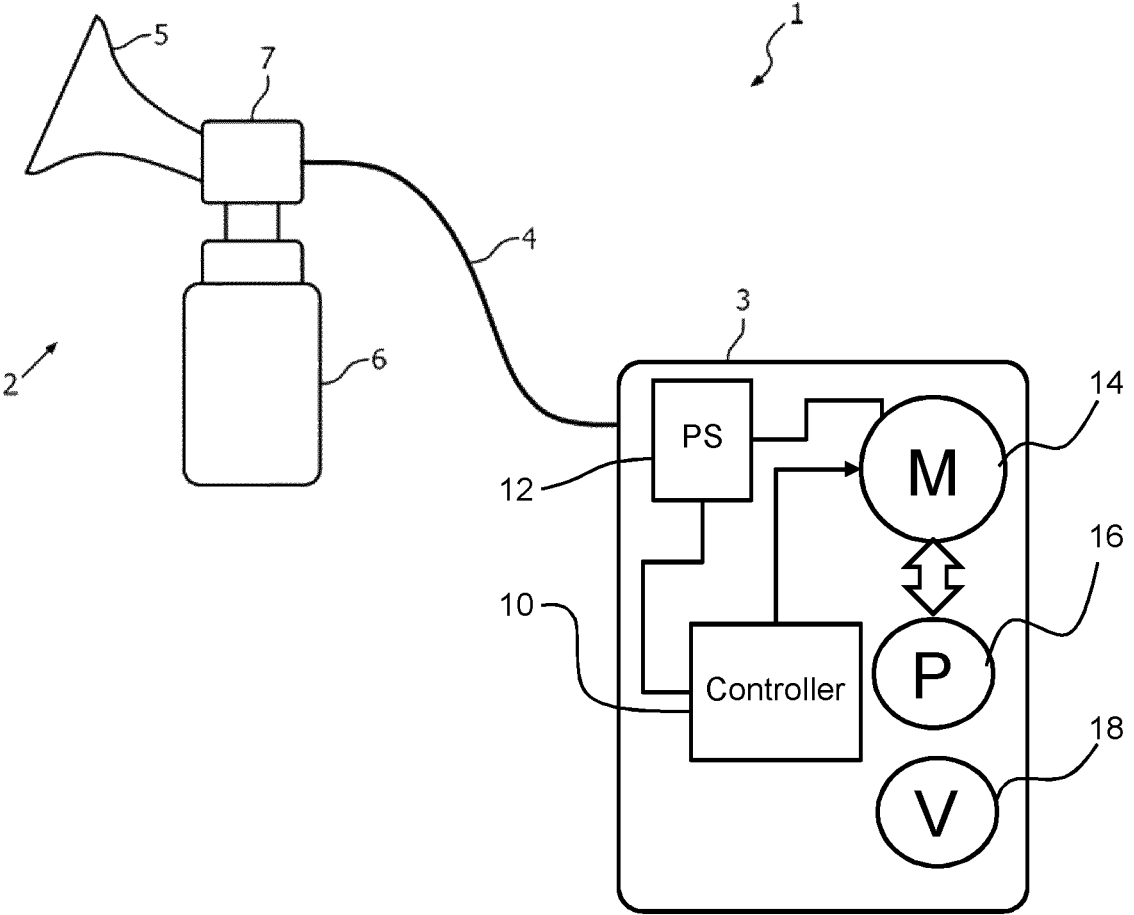
FIG. 1 shows a breast pump system.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a pump arrangement for a breast pump system having a pump motor assembly and a damping arrangement, providing a coupling between an outer surface of the pump motor assembly and an inner surface of a housing for the pump arrangement. A set of one or more limbs extends outwardly from a frame. For example, cushions are formed by a pair of radially extending limbs and a connecting piece connecting to the pair of limbs. This arrangement provides positioning within the housing as well as damping.

FIG. 1 shows a breast pump system 1, comprising an expression unit 2 and a pump arrangement 3 which are connected via a tube 4. The pump arrangement includes various components in addition to the pump, so may be considered to be a general operating unit.

The expression unit 2 is formed with a main body 7, a funnel 5 for receiving a breast of a user and a receptacle 6 for collecting the expressed milk. The funnel 5 and the receptacle 6 are connected to the main body 7. The main body comprises a vacuum chamber. A flexible membrane or diaphragm is located in the vacuum chamber. The membrane prevents expressed milk from flowing into the tube 4 leading to the pump arrangement unit 3.

The pump arrangement 3 may instead be directly mounted and connected to the main body 7. In this case, the membrane prevents expressed milk from flowing directly into the pump arrangement 3.

The pump arrangement 3 comprises a controller 10, a power source 12, a motor 14 and a vacuum pump 16. The controller controls 10 the operation of the power source 12, motor 14 and vacuum pump 16. The pump arrangement 3 further comprises a solenoid valve 18.

In use, the vacuum pump applies a vacuum to the membrane located in the connection member 7 so that it deforms. The membrane deforms to create a vacuum in the funnel 5 which in turns applies a vacuum to the breast which enables milk to be expressed. In one embodiment, the membrane inverts as the membrane deforms. However in an alternative embodiment the membrane does not invert.

Although the breast pump system 1 is described as comprising a membrane such that the vacuum is applied indirectly to the breast, it should be understood that in an alternative embodiment, the vacuum is applied directly to the breast of a user. In this case, the breast pump system does not comprise a membrane and the vacuum created by the vacuum pump is applied directly to the breast.

The vacuum is applied to the breast at intervals. That is, a pressure differential is applied on a cyclic basis. After a vacuum has been established, the pressure from the vacuum is released by the use of the solenoid valve which is temporarily opened. The solenoid valve is an electromechanically operated valve configured to open and close an air passage that connects to the vacuum side of the vacuum pump to ambient air such that when the solenoid valve is closed, the vacuum pump generates a vacuum in the expression unit which enables milk to be expressed from the breast of a user. When the solenoid valve is opened, the vacuum generated by the vacuum pump is released as ambient air flows towards the vacuum or negative pressure created by the vacuum pump such that the pressure exerted on the breast of a user is partially or completely reduced.

This is a basic description of the known operation of a breast pump system. This invention relates in particular the mounting of the motor (or motors) 14 within the housing of the pump arrangement 3. For this reason, further details of the operation of the breast pump system will not be presented.

Figure 2:
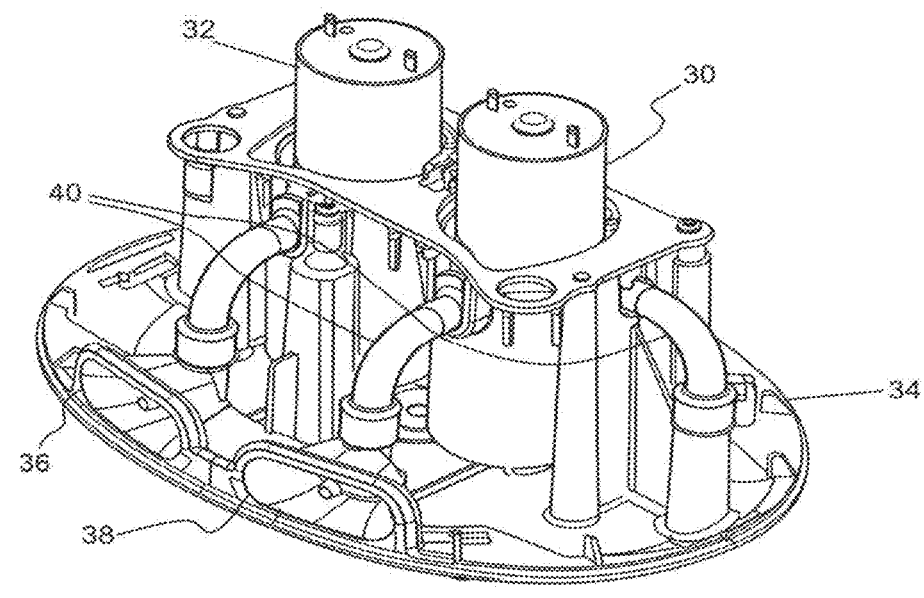
FIG. 2 shows a conventional mounting of the vacuum pump and pump motor to the housing of the pump arrangement.

FIG. 2 shows a conventional mounting of the vacuum pump and pump motor to the housing of the pump arrangement.

This arrangement has two pump motors 30, 32, one for each breast. Thus, this example is for a double assembly, but there may equally be a system with only one pump motor.

The two pump motors are mounted to a supporting frame 34. The supporting frame 34 supports two pump inlets 36, 38 to each of which a respective expression unit 2 connects. Beneath each pump motor 30, 32 is a steel spring (not shown) for damping the vibrations of the pump motor. Flexible tubes 40 allow movement of the pump motors. A first pair of tubes connect to the pump inlets 36, 38 and a second pair of tubes vent to the ambient surroundings.

An outer housing (not shown) is mounted around the outside of the components shown in FIG. 2.

Figure 3:
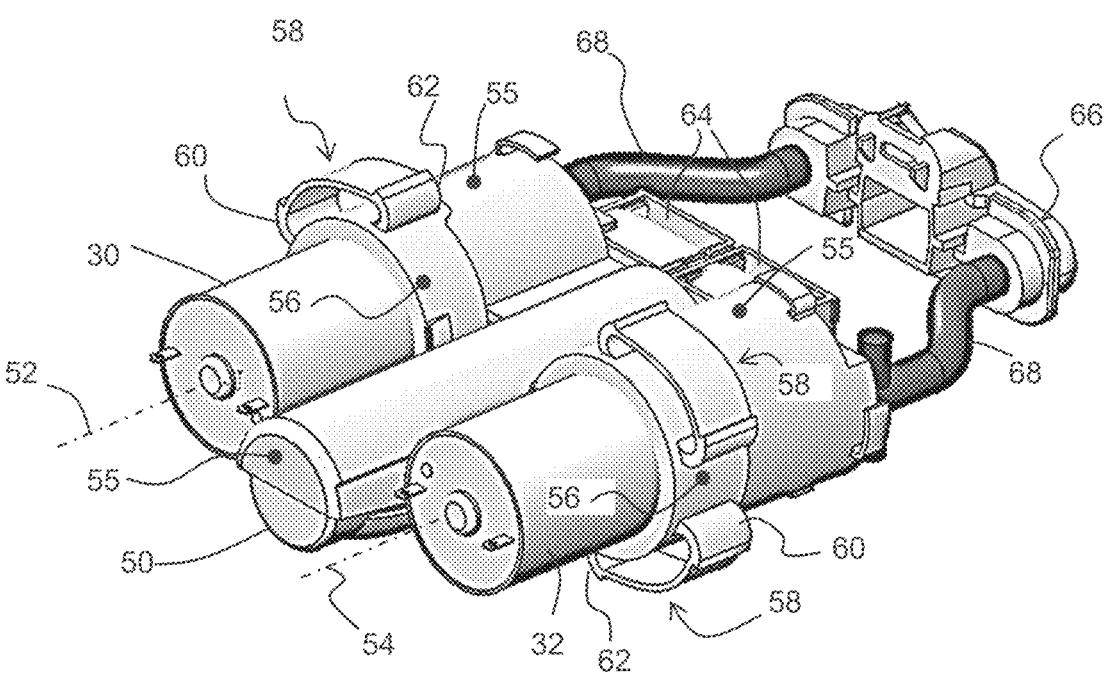
FIG. 3 shows a pump arrangement in accordance with one example of the invention.

FIG. 3 shows a pump arrangement in accordance with one example of the invention.

A two-pump system is again shown, with first and second pump motors 30, 32. A battery unit 50 is also shown mounted between the pump motors, such as a Li-ion rechargeable battery. There are of course also mains operated versions which will not incorporate a battery in which case there is a space between the pump motors (if a modular system is used with the same general design).

There may also be battery and mains versions of a single pump system.

The pump arrangement generally comprises a pump motor assembly comprising a set of one or more pump motors each having an axis 52, 54. This is an axis of rotation of an output shaft of the motor. As stated above, in the example shown, the pump motor assembly has two pump motors 30, 32. A chassis 55 provides support for the pump motors 30, 32 and for the battery 50. Each pump motor has a main body. at one end of the main body, an output shaft projects.

A damping arrangement is coupled to the set of pump motors providing a coupling between an outer surface of the pump motor assembly and an inner surface of the housing (not shown).

The damping arrangement comprises a frame 56 for mounting to each of the pump motors, in particular for mounting to the main body of each of the pump motors, and in the example shown a set of one or more cushions 58 extending outwardly from the outside of the frame 56.

Each cushion 58 comprises at least a first limb 60 which extends at least partly radially outwardly. In the example shown, each cushion also has a second limb 62.

The frame 56 of the damping arrangement may be a single part which connects to the overall pump motor assembly or it may be formed as multiple frame portions. In the example shown, the frame comprises a set of frame portion each in the form of a ring, with one ring for each pump motor. The frame extends (at least) in a plane perpendicular to the axis or set of parallel axes, i.e. it extends around that axis or set of axes.

For example, the pump motors may have a cylindrical outer surface and the ring can be fitted over the pump motor. Alternatively, the ring can be fitted over a portion of the chassis 55 which supports the pump motor or motors.

The cushions 58 provide a coupling between the pump motors and an outer housing, thereby to provide vibration damping (and hence also noise reduction).

This design avoids the need for metal springs as the cushions provide the damping. The cushions suspend the pump motor assembly such that there is no other direct connection that can transmit sound between the pump motor assembly and the housing. The assembly is easy because the frame fits around, or to, the set of pump motors.

The cushion or cushions reduce the amount of space required compared to a steel spring. At the same time, the cushions may be formed of electrically and thermally insulating material giving additional insulating material properties.

The frame and the cushions are formed as a single integral component, such as a molded or extruded component.

FIG. 3 also shows a solenoid valve 64 for each pump motor 30, 32, and an outlet manifold 66. The pump arrangement has two outlet conduits 68 which extend parallel to the axes 52, 54. They position of the pump arrangement in a direction parallel to the axes 52, 54.

The damping arrangement provides control of damping in a plane perpendicular to the axes 52, 54. The use of the conduits 68 to provide positioning in the direction parallel to the axes prevents contact with the housing in that direction and provides vibration damping for the parallel direction.

Figures 4, 5, 6:
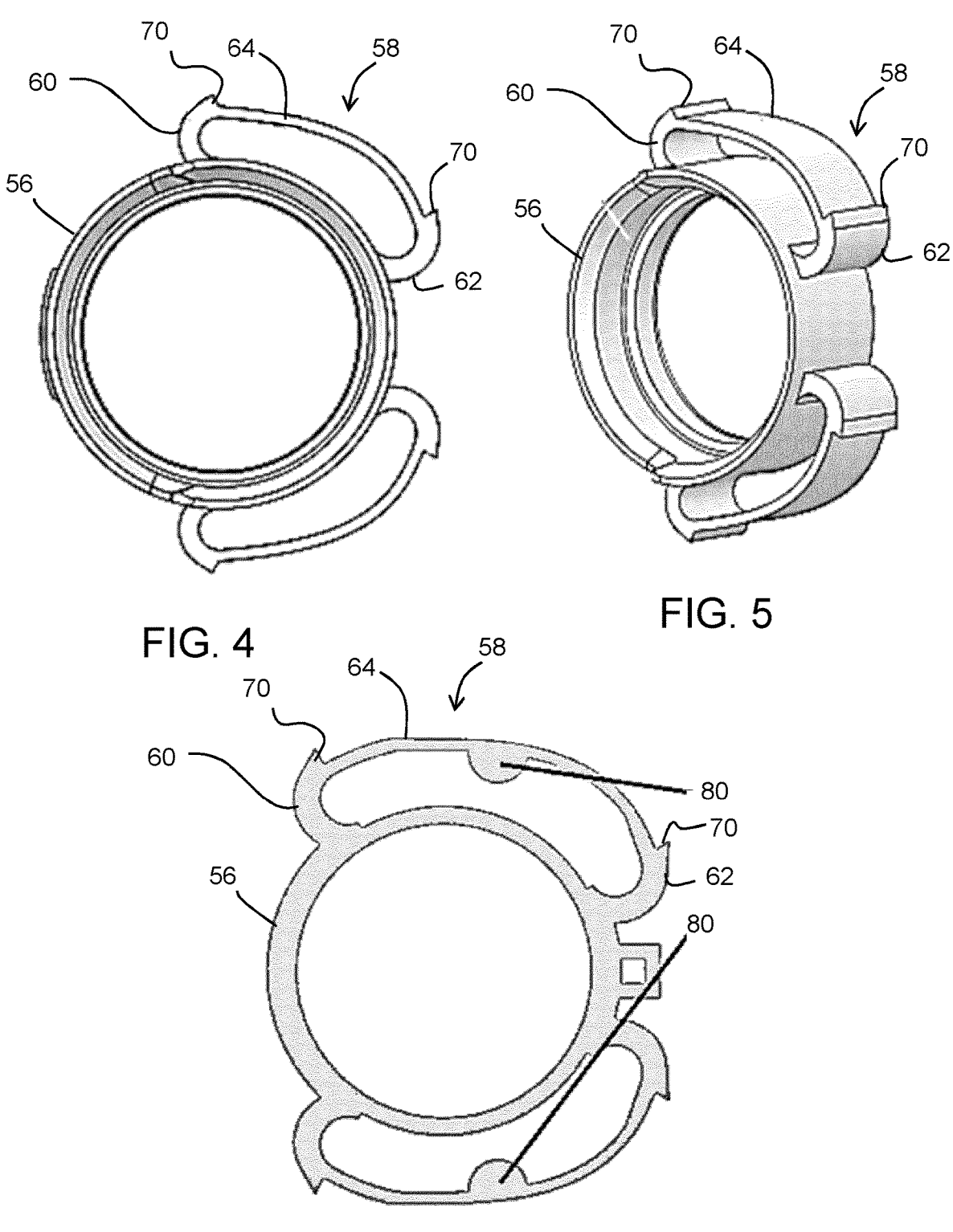
FIG. 4 shows one of the rings in end view.
FIG. 5 shows the ring of FIG. 4 in perspective view.
FIG. 6 shows a modification to the damping arrangement using a stopper.

FIG. 4 shows one of the rings in end view and FIG. 5 shows the ring in perspective view.

It shows more clearly that in this example each cushion 58 comprises first and second limbs 60, 62 which extends at least partly radially outwardly. The two limbs are spaced apart around the ring 56, and a connecting piece 64 connects the radial outermost ends of the first and second limbs 60, 62.

Thus, each cushion comprises a pair of limbs between which a connecting piece extends. The connecting piece couples the limbs together to function as a unit. Each cushion forms a cavity structure with sides (the limbs) and a top (the connecting piece). Each connecting piece is for example radially spaced from the outside of the ring. This forms a cavity between the ring and the connecting piece, which functions as a damping structure. The damping arrangement (the cushion and ring) is for example made of a rubber.

The first and second limbs 60, 62 are shown C-shaped, with the open sides of the two C-shaped limbs facing each other. They may instead be S-shaped. More generally, the first and second limbs are arcuate. The limbs are designed so that they can at least partially collapse by bending, and the arcuate design functions as a pre-bend to provide predictable controlled bending performance. Any arcuate shape may be employed which gives a predictable compression response.

The collapse of the cushions, in particular the radial limbs, provides an end stop feature to ensure that the suspended mass of the pump motor assembly does not cause further damage to other components in the assembly or create loud impact noises every time the assembly faces accelerations when being moved around. The cushion or cushions, in particular the limb or limbs of the cushion or cushions, can for example simply collapse on themselves to provide this end stop.

The combination of the material of the cushion and the specific design of the limb or limbs can be selected to result in specific stiffness and therefore the damping properties can be tuned to the specific mass of the pump motor assembly and other suspended parts.

The radial outermost ends of the limbs may each comprise an alignment feature 70 for aligning with a corresponding alignment feature of the inner surface of the housing. In this way, the limbs provide positioning of the pump arrangement within the outer housing.

FIG. 6 shows a modification to the damping arrangement in which the cushion 58 comprises comprise a stopper 80 formed between the ring and the connecting piece 64. This is used to set the collapse state of the cushion, without requiring any additional parts.

Figure 7:
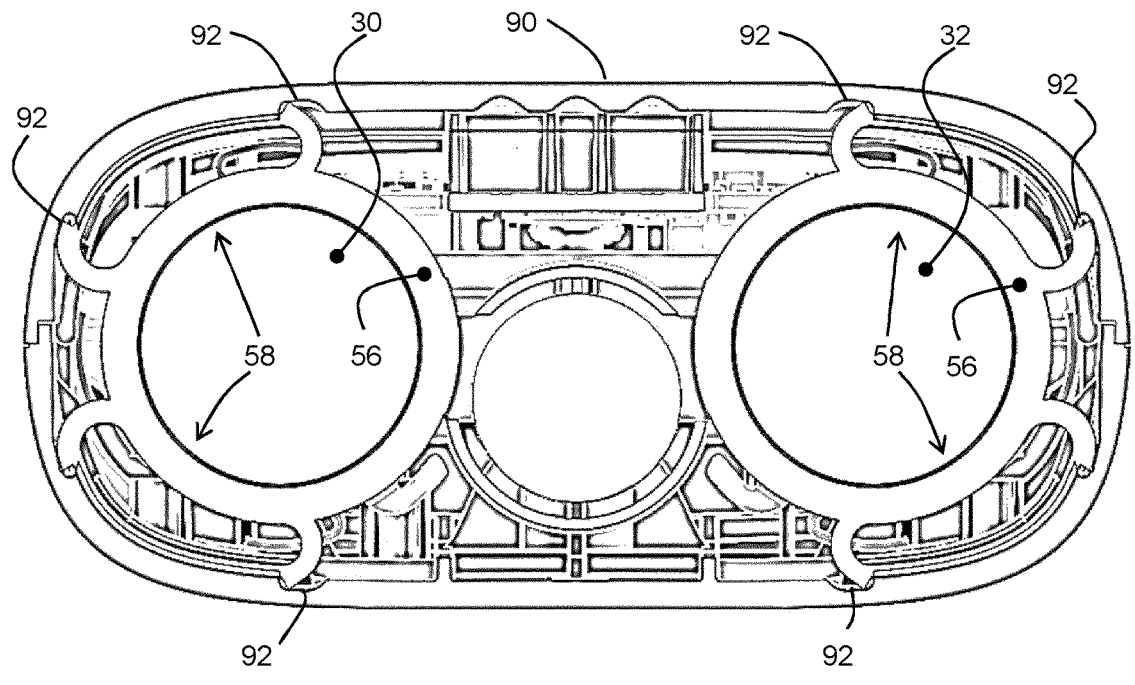
FIG. 7 shows how a double motor version may be mounted in an outer housing.

FIG. 7 shows how a double motor version may be mounted in an outer housing 90. The design shown again has a pump arrangement with two pump motors 30, 32, each with a ring 56 with two cushions 58, such that the pump arrangement has four cushions arranged at corners of a generally rectangular housing shape.

The corners of the cushions engage with slots 92 of the inner surface of the outer housing to provide location of the pump arrangement. In this example, there is a ring arrangement of two rings 56; one for each pump motor and each having a set of two cushions.

Figure 8:
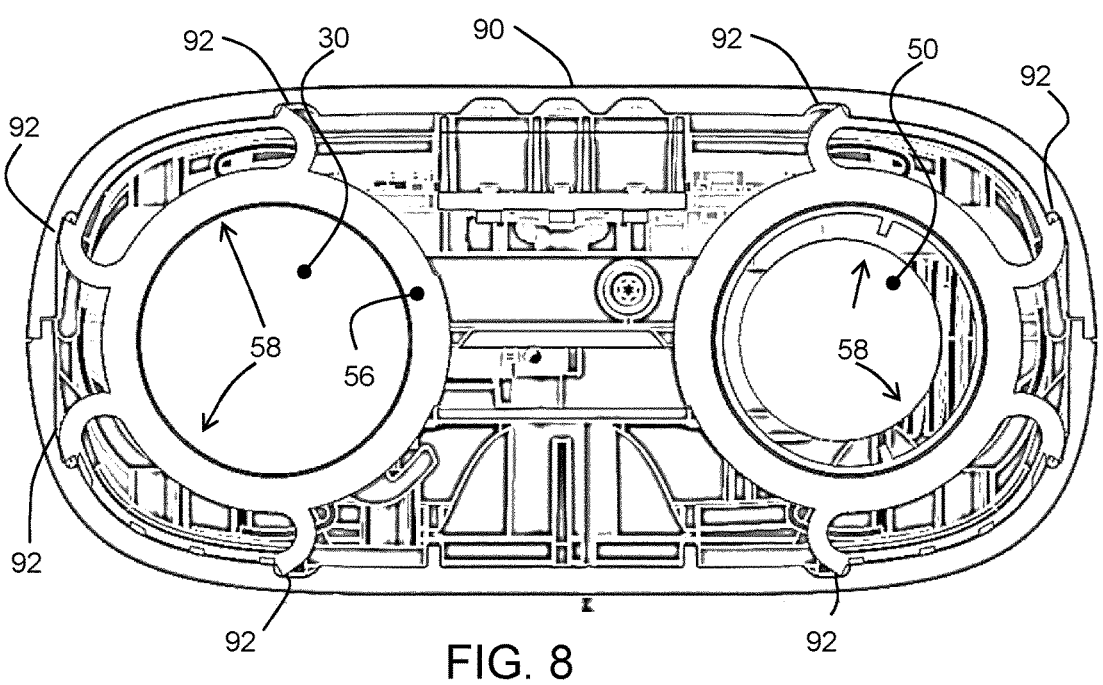
FIG. 8 shows an alternative design with only one motor and a battery.

FIG. 8 shows an alternative design with only one motor 30 and a battery 50. The battery also has a damping ring.

Figures 9, 10:
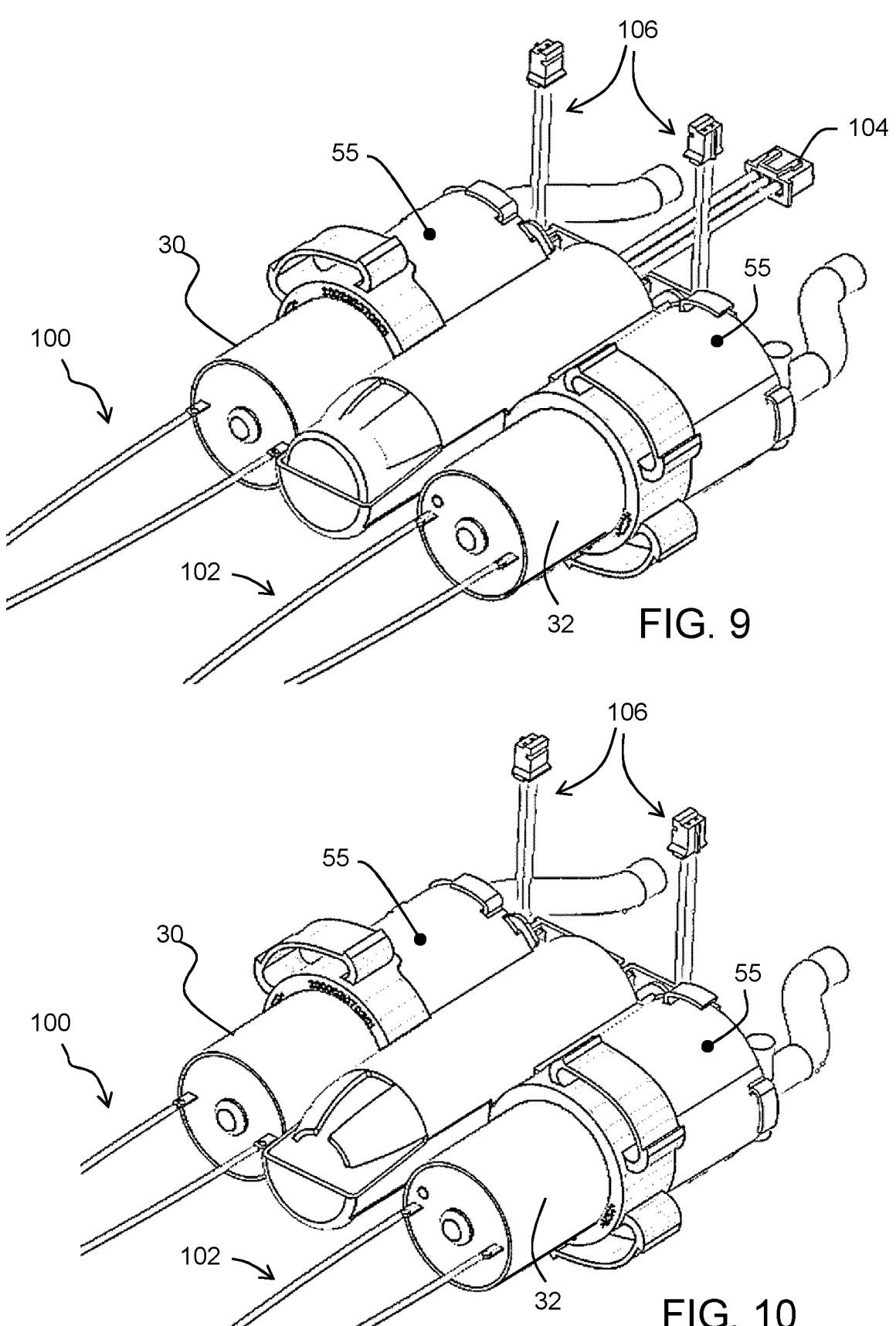
FIG. 9 shows the design of FIG. 3 with the electrical connections.
FIG. 10 shows the design based on FIG. 9 with no battery, but sharing the same chassis design.

FIG. 9 shows the design of FIG. 3 with the electrical connections. A first wire pair 100 connects to the first pump motor 30, a second wire pair 102 connects to the second pump motor 32, a charging cable 104 connects to the battery 50 and control lines 106 connect to the solenoids 64.

FIG. 10 shows the design based on FIG. 9 with no battery, but sharing the same chassis design.

Figures 11, 12:
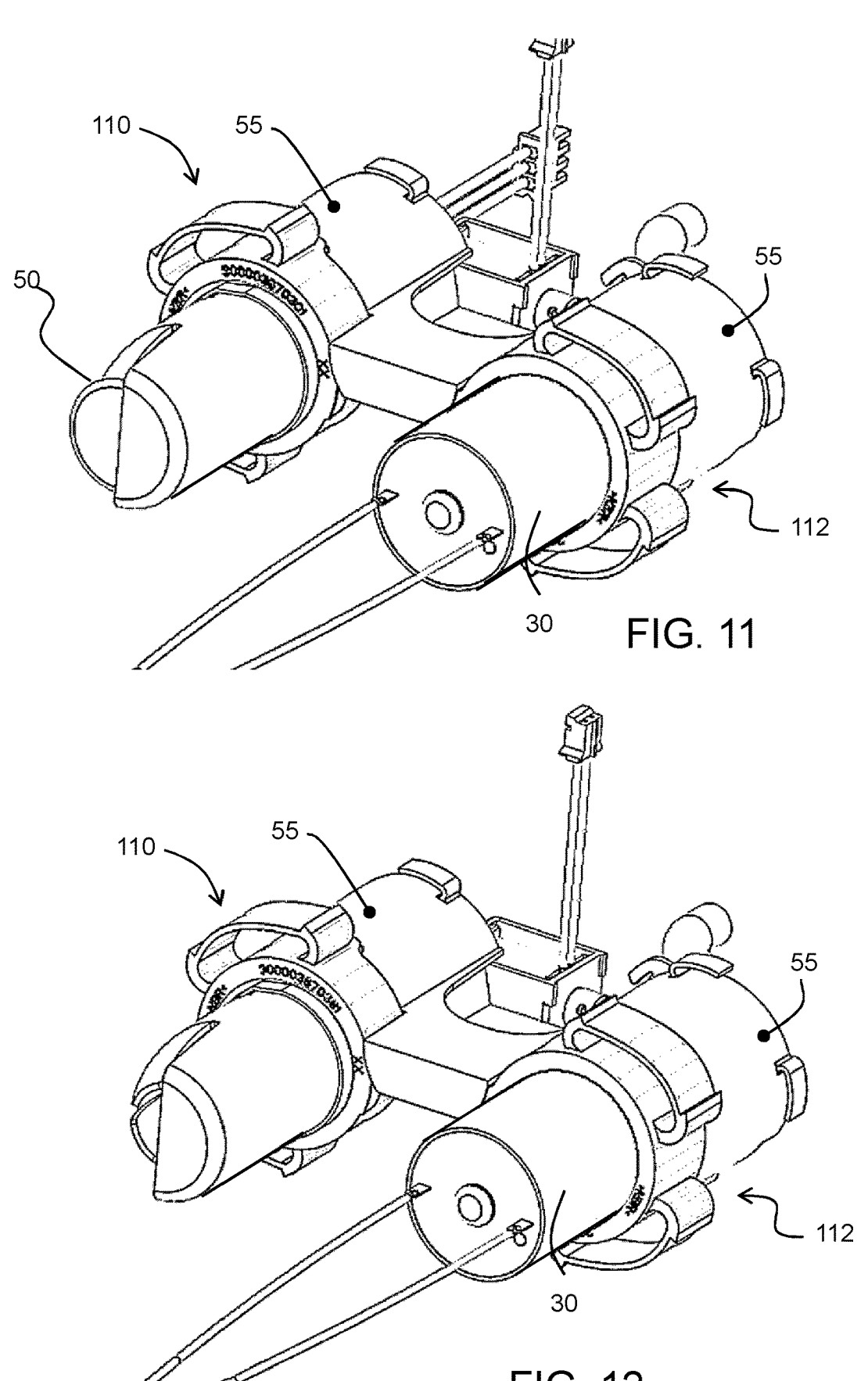
FIG. 11 shows a different chassis design with one damping ring attached to the chassis around the battery and one damping ring attached to the chassis around the single pump motor.
FIG. 12 shows the design based on FIG. 11 with no battery, but sharing the same chassis design.

FIG. 11 shows a different chassis design with one damping ring 110 attached to the chassis 55 around the battery 50 and one damping ring 112 attached to the chassis around a single pump motor 30.

FIG. 12 shows the design based on FIG. 11 with no battery, but sharing the same chassis design.

Figure 13:
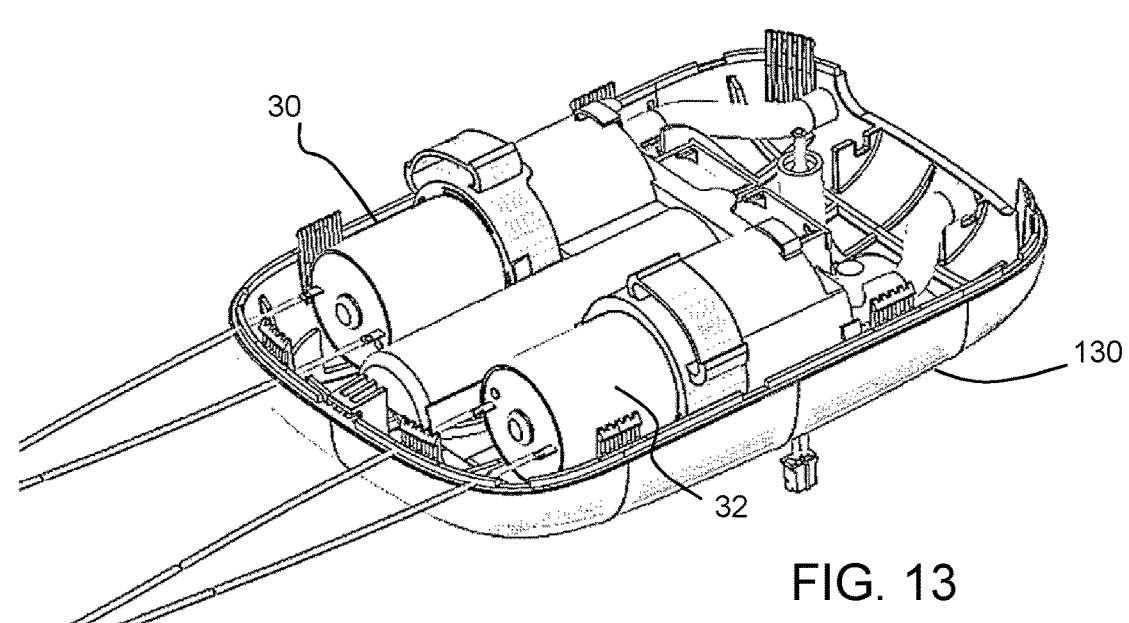
FIG. 13 shows the design of FIG. 9 mounted in a lower half casing of the outer housing.

FIG. 13 shows the design of FIG. 9 mounted in a lower half casing 130 of the outer housing.

Figure 14:
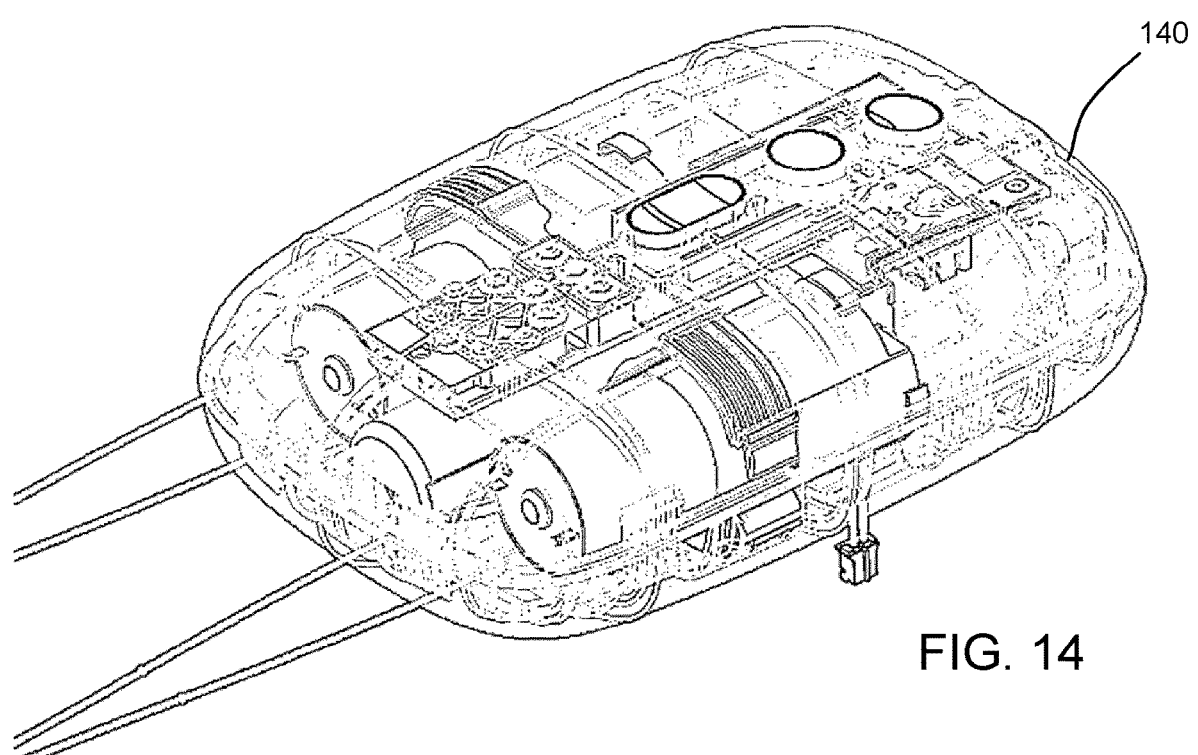
FIG. 14 shows the design of FIG. 13 with the upper half casing fitted over the lower half casing.

FIG. 14 shows the design of FIG. 13 with the upper half casing 140 fitted over the lower half casing.

Figure 15:
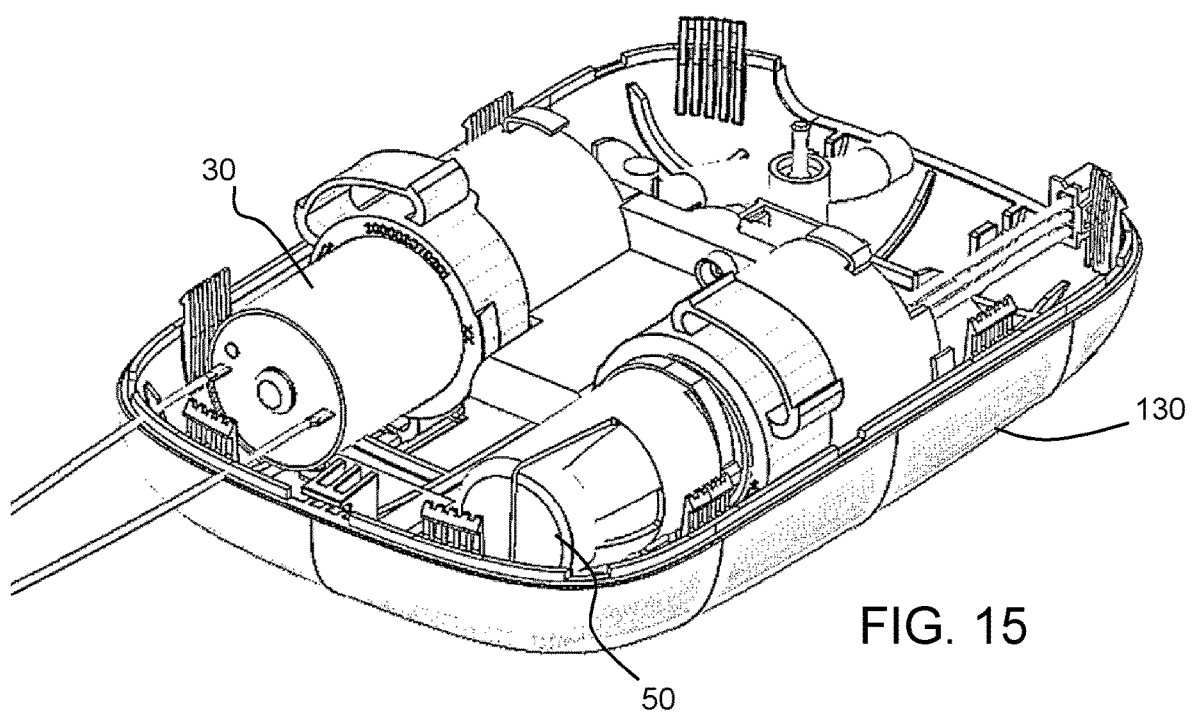
FIG. 15 shows the design of FIG. 11 mounted in a lower half casing of the outer housing.

FIG. 15 shows the design of FIG. 11 mounted in a lower half casing of the outer housing.

Figure 16:
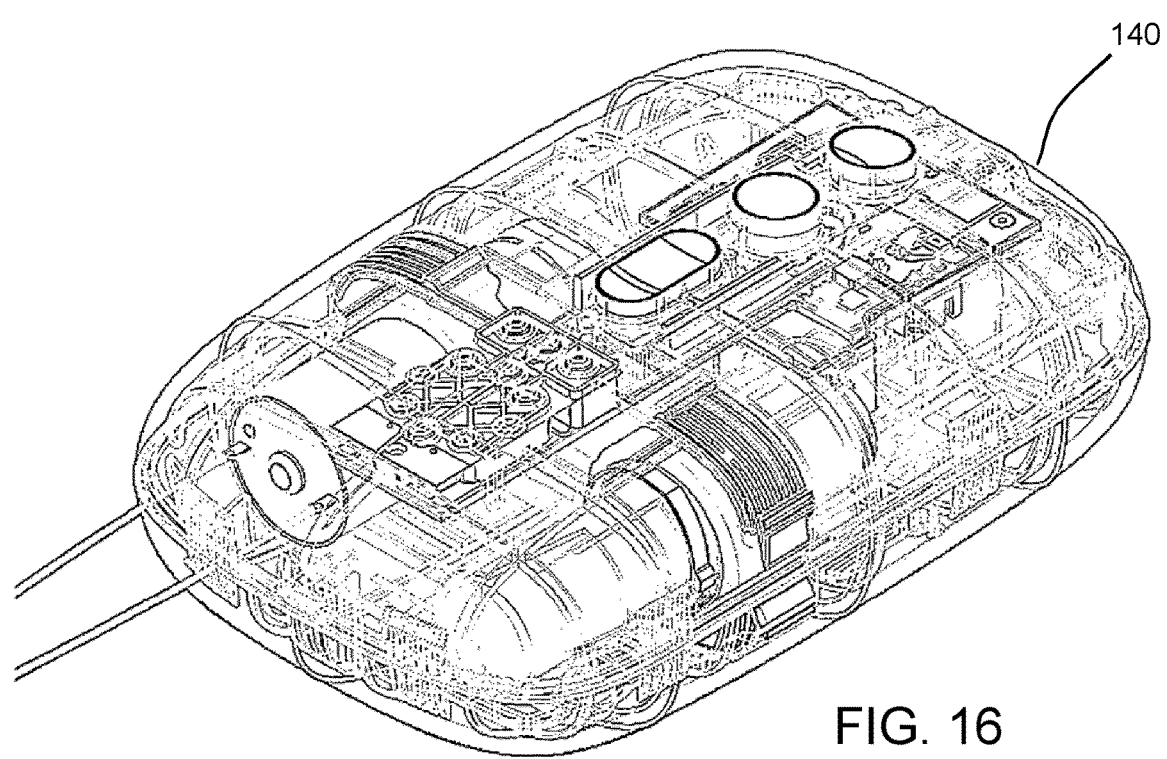
FIG. 16 shows the design of FIG. 15 with the upper half casing fitted over the lower half casing.

FIG. 16 shows the design of FIG. 15 with the upper half casing fitted over the lower half casing.

The examples above all make use of damping arrangements of multiple separate rings each with a pair of cushions. However, many other designs are possible. FIGS. 17 to 20 show various alternative designs.

Figures 17, 18, 19, 20:
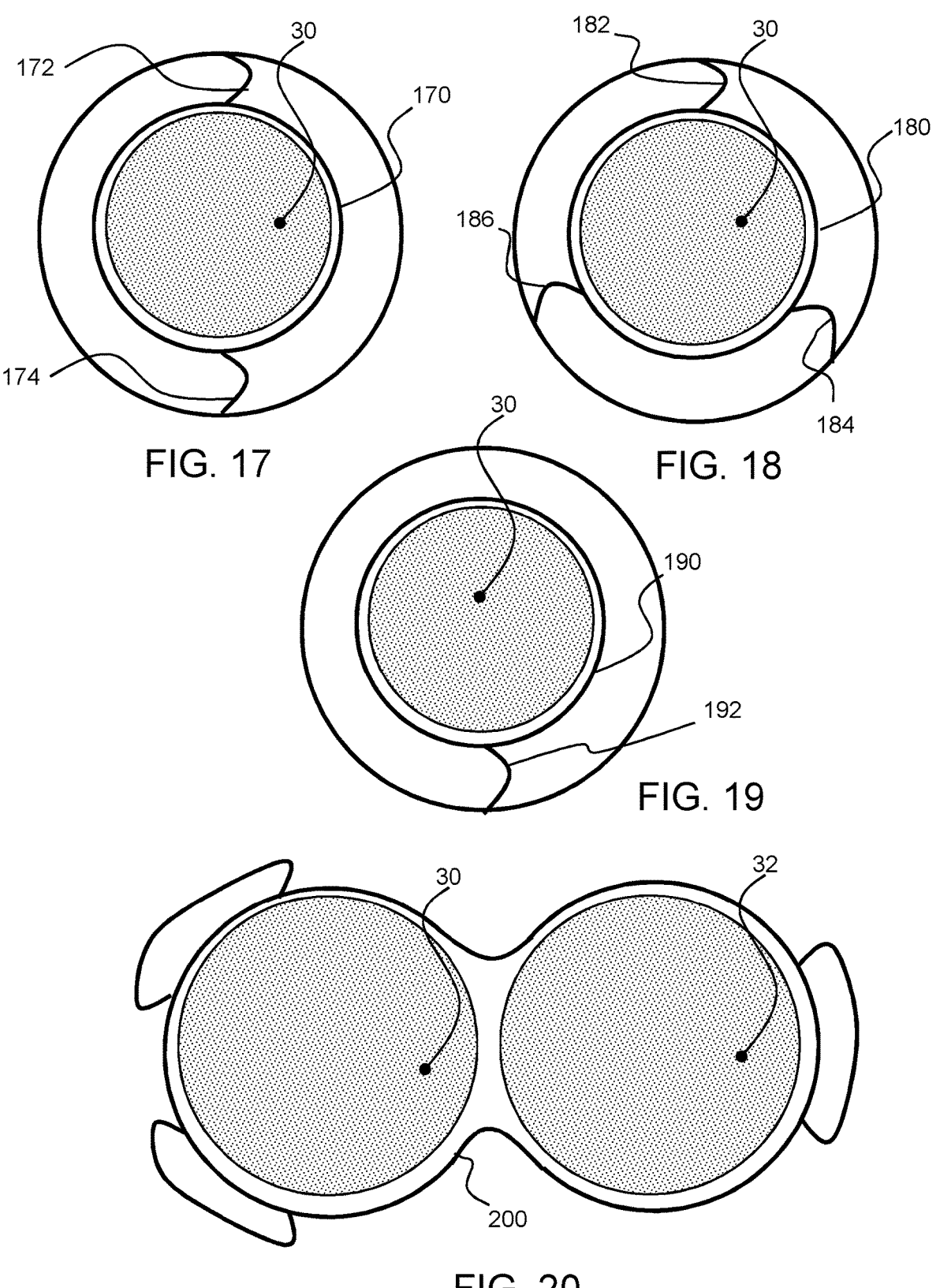
FIGS. 17 to 20 show various alternative designs.

FIG. 17 shows a single pump motor 30 around which is a frame 170 (in the form of a ring) and two cushions extending outwardly from the outside of the frame. In this case, the two cushions share first and second limbs 170, 172 so there is only one limb per cushion, and the two cushions together form a full annulus.

FIG. 18 shows a single pump motor 30 around which is a frame 180 (in the form of a ring) and three cushions extending outwardly from the outside of the frame. In this case, the three cushions share first to third limbs 180, 182, 184 so there is only one limb per cushion, and again the three cushions together form a full annulus.

FIG. 19 shows a single pump motor 30 around which is a frame 190 (in the form of a ring) and one cushion extending all around the frame supported by only single limb 192.

FIG. 20 shows two pump motors 30, 32 (or the same design could be used for one pump motor and one battery) in which the frame 200 is a single unit around the assembly of both pump motors. There are three cushions in this design.

It will be seen from the examples above that the frame (the ring or rings) may be fitted around the pump motor or around a chassis which may itself extend around the pump motor or around other components such as a battery. The rings do not need to fully surround the motor or chassis—they could simply clip on laterally rather than sliding on axially.

The damping arrangement may support not only the pump motor or motors, but also any other parts associated with the same chassis or sub-assembly within the housing that requires isolation and damping. These parts may include solenoid valves etc.

The invention provides a simple, low cost, easy to assemble suspension design as an alternative to using springs with complex assembly steps. In addition to sound reduction, the damping arrangement also provides protection against impact and/or external vibrations.

The performance of the suspension in terms of damping frequencies and accelerations is determined by:

the suspension component design (thickness of the limbs, material properties (especially shore hardness), number of limbs, profile of the limbs, wall thickness, range of travel during compression, width of limbs/cushions, positions of limbs/cushions (with respect to the center of mass, for example), orientation of the limbs/cushion and any pre-tension designed into the structure);

the suspended mass;

the available space.

The invention enables the space occupied by the entire assembly to be reduced, e.g. from 301470 mm$^3$ for a conventional suspension system consisting of springs and tubes to 104370 mm$^3$ for an otherwise equivalent design. This reduces the space occupied by more than half (per pump motor), and more importantly, allows for freedom to create a more compact breast pump, giving the advantage of portability to the user.

The arrangement of the invention uses one suspension part per pump motor, giving advantages in terms of cost and risk reduction. Fabrication costs and assembly costs are reduced (by lowering assembly time) and the risk of wrong assembly and failures is reduced.

As explained above, the damping arrangement is the primary suspension system, but the pump tubing may be used to provide a secondary function as an additional suspension element. However, even without use of the tubing, the damping arrangement is able to support and isolate the pump assembly from the surroundings in terms of noise and vibrations.

The (at least partially) radial limb or limbs provide the desired elasticity. Most simple rubber materials are elastic in the general sense, but they do not provide sufficient isolation on their own. The invention provides spring like loading using the radial limbs, and they can be optimized in terms of shape and dimensions for a desired spring function.

The examples above all provide cushions having at least one limb and an outer connecting piece. However, as a minimum there may be only the limbs (and no connecting pieces). The limbs provide the required collapse performance and also provide alignment with the housing. The limbs are then integral with the frame. By forming cushions (by connecting adjacent pairs of limbs) a more stable structure is formed which may provide more controllable damping performance.

The limbs may have a constant cross sectional shape along one axis and hence can be 2D extruded, but more complex 3 dimensional structures are possible, for example rotated about a central axis.

The ring design shown enables easy mounting over cylindrical pump motors or chassis parts. The alignment features enable automatic location in the outer housing giving short assembly time since.

The overall noise and vibration emanating from a product is a complex function of the motor and solenoid operations, the suspension system and the housing design.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

The invention claimed is:

1. A pump arrangement for a breast pump system, comprising:

a housing;

a pump motor assembly comprising a pump motor with an axis or a set of pump motors with parallel axes; and a damping arrangement coupled to the pump motor assembly and providing a coupling between an outer surface of the pump motor assembly and an inner surface of the housing, wherein the damping arrangement comprises:

a frame for coupling to the pump motor assembly, wherein the frame comprises a ring arrangement which:

extends around the pump motor; or extends around each pump motor of the set of pump motors; or extends around an overall assembly of the set of pump motors, wherein the frame extends in a plane perpendicular to the axis or set of parallel axes;

a set of one or more first limbs extending at least partially radially in a direction extending outwardly from the axis or one of the set of parallel axes from outside of the frame, and a set of one or more second limbs extending at least partially radially outwardly from an outside of the frame, wherein a connecting piece is present between a pair of first and second limbs spaced apart around the frame, such that a pair of first limbs and second limbs and the connecting piece form a cushion, wherein:

each of the set of one or more first limbs and each of the set of one or more second limbs is C-shaped, with open sides of a pair of C-shaped limbs facing each other, or each of the set of one or more first limbs and each of the set of one or more second limbs is S-shaped.

2. The pump arrangement as claimed in claim 1, wherein radial outermost ends of the set of one or more first limbs each comprise an alignment structure for aligning with a corresponding alignment structure of the inner surface of the housing.

3. The pump arrangement as claimed in claim 1, wherein the first and second limbs of each pair are arcuate.

4. The pump arrangement as claimed in claim 1, wherein radial outermost ends of the set of one or more first limbs and radial outermost ends of the set of one or more second limbs each comprise an alignment structure for aligning with a corresponding alignment structure of the inner surface of the housing.

5. The pump arrangement as claimed in claim 1, wherein the pump arrangement includes four pairs of first and second limbs, each pair of first and second limbs having an associated connecting piece forming a cushion.

6. The pump arrangement as claimed in claim 1, wherein each connecting piece is radially spaced from the an outside of the frame.

7. The pump arrangement as claimed in claim 1, wherein the cushion comprises a stopper formed between the frame and the connecting piece.

8. The pump arrangement as claimed in claim 1, wherein the pump motor assembly comprises the set of pump motors and the ring arrangement comprises a respective ring around each pump motor of the set of pump motors.

9. The pump arrangement as claimed in claim 1, wherein the damping arrangement is made of an elastically deformable material.

10. The pump arrangement as claimed in claim 1, wherein the pump motor assembly comprises two pump motors, each with a separate frame comprising a ring arrangement with two cushions, such that the pump arrangement has four cushions arranged at corners of a rectangle.

11. The pump arrangement as claimed in claim 1, wherein the pump arrangement has an inlet conduit and an outlet conduit, wherein the inlet and outlet conduits extend parallel to the axis or set of axes and provide positioning of the pump arrangement in a direction parallel to the axis or set of axes.

12. The pump arrangement as claimed in claim 1, wherein the ring arrangement extends around a main body of the pump motor, around a main body of each pump motor of the set of pump motors, or around the main bodies of an overall assembly of the set of pump motors.

13. A breast pump system comprising:

an expression unit; and a pump arrangement as claimed in claim 1.

\* \* \* \* \*